United States Patent [19]

Yamada et al.

[11] Patent Number: 5,334,519

[45] Date of Patent: Aug. 2, 1994

[54] PROCESS FOR BIOLOGICAL PRODUCTION OF AMIDES WITH R. RHODOCHROUS J-1

[75] Inventors: Hideaki Yamada; Toru Nagasawa, both of Kyoto, Japan

[73] Assignee: Nitto Kagaku Kogyo Kabushiki Kaisha, Tokyo, Japan

[21] Appl. No.: 777,641

[22] Filed: Oct. 15, 1991

Related U.S. Application Data

[63] Continuation of Ser. No. 243,986, Sep. 13, 1988, abandoned.

[30] Foreign Application Priority Data

Sep. 18, 1987 [JP] Japan .............................. 62-234597
Mar. 26, 1988 [JP] Japan .............................. 63-72766

[51] Int. Cl.$^5$ .................... C12N 1/20; C12N 1/38; C12P 13/02
[52] U.S. Cl. .................... 435/129; 435/252.2; 435/252.1; 435/244
[58] Field of Search ............ 435/129, 872, 863, 252.2, 435/252.1, 244

[56] References Cited

U.S. PATENT DOCUMENTS

4,629,700 12/1986 Prevatt .................... 435/128
5,135,858 8/1992 Yamada .................... 435/106

OTHER PUBLICATIONS

Demain et al., "Industrial Microbiology and Technology", p. 103, 1986, ASM.
Harper, D. B., Biochem J., 1977, vol. 165, pp. 309–319.
Goodfellow et al. "The Biology of Actinomycetes", 1984, Academic Press, pp. 91–94.
Nagasawa et al. Nitrile Hydratase-catalyzed Production of Nicotinamide from 3-Cyanopyridine in Rhodococcus rhodchrous J1, Applied and Environmental Microbiology, vol. 54, No. 7 pp. 1766–1769, @Jul. 1988, Department of Agricultural Chemistry, Kyoto University, Kitashirakawa, Oiwake-Cho, Sakyo-ku, Kyoto 606, Japan.
Nagasawa et al., Occurrence of a Cobalt-Induced and Cobalt-Containing Nitrile Hydratase in Rhodococcus rhodochrous J1, Biochemical and Biophysical Research Communications, vol. 155, pp. 1008–1016, Academic Press, @Sep. 15, 1988. Department of Agricultural Chemistry, Kyoto University, Kitashirakawa Oiwake--cho, Sakyo-ku, Kyoto 606, Japan.
Collins et al., The Utilization of Nitriles by Nocardia rhodochrous, Journal of General Microbiology, pp. 711–718, @ 1983, (Printed in Great Britain), Biological Laboratory, University of Kent, Canterbury, Kent CT2 7NJ U.K.
Mayger et al., Nitrile Hydratase-Catalyzed Production of Isonicotinamide, Picolinamide and Pyrazinamide from 4-Cyanopyridine, 2-Cyanopyridine and Cyanopyrazine in Rhodococcus thodochrous J-1, Journal of Biotechnology, 8, @ 1988, Department of Agricultural Chemistry, Kyoto University, Kitashirakawa Sakyo-ku, Kyoto 606, Japan.
Asano, et al., Aliphatic Nitrile Hydratase from Arthrobacter Sp. J-1 Purification and Characterization, Agric. Biol. Chem., 46, pp. 1165–1174, 1982, Department of Agricultural Chemistry, Kyoto University, Kyoto 606, Japan.

Primary Examiner—Irene Marx
Attorney, Agent, or Firm—Emmanuel J. Lobato; Robert E. Burns

[57] ABSTRACT

In a process for biological production of an amide wherein a nitrile is hydrated into a corresponding amide by the action of a nitrile hydratase originated in a microorganism, the improvement which comprises the use of nitrile hydratase which is obtained by culturing a microorganism of the species *Rhodococcus rhodochrous* in the presence of a cobalt ion.

Aromatic nitriles such as a cyanopyridine as well as aliphatic nitrile such as acrylonitrile are hydrated into the corresponding amides.

9 Claims, No Drawings

PROCESS FOR BIOLOGICAL PRODUCTION OF AMIDES WITH *R. RHODOCHROUS* J-1

This is a continuation of copending application Ser. No. 07/243,986, filed Sep. 13, 1988 and now abandoned.

BACKGROUND OF THE INVENTION

1. Field of the Art

The present invention relates to a process for hydrating a nitrile thereby converting it into a corresponding amide by the action of a nitrile hydratase originated in a microorganism. More particularly, the present invention relates to a process for biologically producing an amide characterized by the microorganism used and a method for producing nitrile hydratase.

2. Background Art

A lower aliphatic amide such as acrylamide is produced by the hydration of a nitrile such as acrylonitrile, and there have been proposed many methods of hydration by the action of enzymes such as nitrilase or nitrile hydratase produced by microorganisms (see, for example, Japanese Patent Publication No.21519/87, U.S. Pat. No.4,001,081; Unexamined Published Japanese Patent Application Nos. 162193/86 and 91189/87, EPC Nos. 0188316 and 0204555; and Japanese Patent Publication Nos. 17918/81 and 37951/84, U.S. Pat. Nos.4,248,968 and 4,637,982). Such methods for biologically producing an amide have also been used commercially and have attracted attention as being advantageous processes for producing acrylamide.

Several microorganisms have already been proposed as the ones used for the process for biologically producing an amide. However, as far as the present inventors have researched, these microorganisms, although effective for the hydration of lower aliphatic nitriles, are not always effective for the hydration of aromatic nitriles. Thus, the method for producing nicotinamide by the hydration of 3-cyanopyridine exhibits too low a yield to use for commercial purposes.

The prior art to carry out the culture of microorganism in the presence of an iron ion or a manganese ion is known. This technique is utilized also in the process for biologically producing an amide, and examples for culturing the microorganisms of genus Rhodococcus in the presence of an iron ion are disclosed in Unexamined Published Japanese Patent Application Nos. 162193/86 and 91189/87.

As a result of the research conducted by the present inventors, it was found that a nitrile hydration enzyme, i.e., nitrile hydratase, originated in a bacterium of genus Pseudomonas contains $Fe^{+++}$ in its active center and thus the presence of an iron ion in a culture medium is essential to the culture of the microorganism. Accordingly, it is also presumed in the case of the microorganism of genus Rhodococcus in the known examples described above that an iron ion in the culture medium for culturing the microorganism is essential to the production of a nitrile hydration enzyme.

SUMMARY OF THE INVENTION

According to the present invention, it has been discovered that a specific strain of genus Rhodococcus, i.e. a strain J-1 of the species rhodochrous does not produce nitrile hydratase in an iron ion containing culture medium and it is in a cobalt ion containing culture medium that the strain produces nitrile hydratase; and that the nitrile hydratase thus produced can utilize an aromatic nitrile as a substrate so it is transformed into an amide.

Accordingly, the process for producing an amide according to the present invention is a process for biological production of an amide wherein a nitrile is hydrated into a corresponding amide by the action of a nitrile hydratase originated in a microorganism, characterized in that said nitrile hydratase is obtained by culturing a microorganism of the species *Rhodococcus rhodochrous* in the presence of a cobalt ion.

According to the present invention, although there is zero nitrile hydratase activity in an iron ion containing culture medium, the activity will be developed in a culture medium which contains cobalt ion. It would be considered unexpected that the development of nitrile hydratase of this specific microorganism has critical dependency on the type of metal ion in a culture medium.

Furthermore, according to the present invention, hydration of an aromatic nitrile can be conducted advantageously. The effect of the present invention is useful because of the importance of nicotinamide, that is the hydration product of 3-cyanopyridine, as a raw material for vitamin synthesis or of pyrazineamide, that is the hydration product of cyanopyrazine, useful as a tuberculostat.

DETAILED DESCRIPTION OF THE INVENTION

1. Some General Concept of a Process for Biologically Producing an Amide

The present invention is concerned with a process for hydrating a nitrile to convert it into a corresponding amide by the action of a nitrile hydratase originated in a microorganism, which process comprises basically the culturing of a microorganism, the inducing of a nitrile hydratase and the causing the nitrile hydratase thus obtained to act upon a substrate nitrile.

These steps per se are known as unit operations and are used in their suitable form in the present invention. The phraseology "nitrile hydratase is obtained by culturing a microorganism in the presence of a cobalt ion" takes the induction of a nitrile hydratase as a natural premise.

The premise of the present invention "a process for hydrating a nitrile to convert it into a corresponding amide by the action of a nitrile hydratase originated in a microorganism" includes any appropriate embodiments or variations for causing the nitrile hydratase to act upon the nitrile. As one of such embodiments, there is a method for collecting an enzyme produced by a microorganism and using the enzyme as an enzyme preparation. This way of use of the nitrile hydratase, wherein the enzyme is used as an enzyme preparation, is to be understood as falling within a category of "a process for biologically producing" in the present invention.

2. Details of the Hydration Reaction

1) Microorganism

The microorganism used in the present invention is a microorganism of a species *Rhodococcus rhodochrous.*

Representative strain of this species is the strain J-1.

Details of the strain J-1 is as follows:

(1) Origin and deposition

The strain J-1 was sampled from the soil in Sakyo-ku of Kyoto, Japan, and deposited as an international deposit (under the Budapest Treaty on the International Recognition of the Deposit of Microorganisms for the Purposes of Patent Procedure) in Fermentation Research Institute, Japan, Agency of Industrial Sciences and Technology with the accession number of FERM BP-1478.

(2) Bacteriological properties
(a) Morphology
(1) Form and size of cells: 0.9 - 1.0 $\mu$ × 3 - 10 $\mu$.
(2) Presence of polymorphism of cells: The cell exhibits a long rod shape in the initial stage of culture, grows with snapping in the shape of curvature and then is divided into short bacilli.
(3) Motility: None.
(4) Presence of spores: None.
(5) Gram's stainability: Positive.
(6) Acid-fast property: Negative.
(7) Heterophile granulocyte: Detected.
(b) Growing states in various culture media (30° C.)
(1) Broth agar plate culture: Circle with a diameter of 1 mm ( 48 hours ), irregular and smooth, the surface being rather dry, flat, opaque, pale orange-pink color.
(2) Broth agar slant culture: Thread with a smooth surface being rather dry, section slightly protruding with rather dry, pale orange-pink color.
(3) Broth liquid culture: Flourishing growth, forming the bacterial cell membrane , and moderate turbidity and sediment are formed accompanying the growth.
(4) Broth gelatin stab culture: Growing finely on the surface, in the shape of a cone along the stab part, but not in the lower layer; liquefaction is not observed in gelatin.
(5) Litmus milk: No change.
(c) Physiological properties
(1) Reduction of nitrates: Positive.
(2) Denitrification: Negative.
(3) MR test: Negative.
(4) VP test: Negative.
(5) Generation of indole: Positive.
(6) Generation of hydrogen sulfide: Positive.
(7) Hydrolysis of starch: Negative.
(8) Utilization of citric acid:
   Kocur's culture medium: Negative.
   Christensen's culture medium: Positive.
(9) Utilization of inorganic nitrogen source:
   nitrate: Positive.
   ammonium salt: Positive.
(10) Generation of coloring
   matter: Negative.
(11) Urease: Positive.
(12) Oxidase: Negative.
(13) Catalase: Positive.
(14) Hydrolysis of cellulose: Negative.
(15) Range of growth: pH: 5 - 10, temperature: 10+–41° C.
(16) Attitude to oxygen: Aerobic.
(17) Decomposition of tyrosine: Positive.
(18) Decomposition of adenine: Positive.
(19) Phosphatase: Positive.
(20) Hydrolysis of Tween 80: Positive.
(21) O—F test: Negative.
(22) Heat resistance (in 10% skim milk at 72° C. for 15 minutes): None.
(23) Generation of an acid and gas form a sugar:

|  | Acid | Gas |
|---|---|---|
| L-Arabinose | − | − |
| D-Xylose | − | − |
| D-Glucose | + | − |
| D-Mannose | − | − |
| D-Fructose | + | − |
| Maltose | + | − |
| Sugar | + | − |
| Lactose | − | − |
| Trehalose | − | − |
| D-Sorbitol | + | − |
| D-Mannitol | + | − |
| Glycerol | + | − |

+: positive;
−: negative

(24) Growth in a single carbon source:

| (24)Growth in a single carbon source: | |
|---|---|
| Inositol | − |
| Maltose | + |
| D-Mannitol | + |
| Rhamnose | − |
| D-Sorbitol | + |
| m-Hydroxybenzoic acid | + |
| Sodium adipate | + |
| Sodium benzoate | + |
| Sodium citrate | + |
| Sodium lactate | + |
| Testotetrone | + |
| L-Tyrosine | + |
| Glycerol (1%) (w/v) | (+) |
| Trehalose | (+) |
| p-Hydroxybenzoic acid (1%) (w/v) | + |

+: positive;
−: negative
(+): slightly positive.

(25) Fatty acid and analysis of
   cell wall: Containing unsaturated and saturated straightchain fatty acids and tuberculo-stearic acid. TLC of mycolic acid gives single spot.

As a result of classification of the above described bacteriological properties in the light of the Bergy's Manual of Systematic Bacteriology, the strain J-1 is an aerobic, Gram-positive, weak acid-fast, catalase-positive and non-endospore generating bacillus, which will not insert flagellum. It also exhibits a shape of an elongated bacillus like a mycelium in the initial stage of growth, grows with branching and then divided into short bacilli. Therefore, it is recognized to belong to a bacterium of a Nocardia type.

The analysis of fatty acid composition exhibits that the bacterium contains unsaturated and saturated straight-chain fatty acids containing tuberculostearic acid. The TLC analysis of mycolic acid gives a single spot having the same Rf value as of the standard bacterium *Rhodococcus rhodochrous* (IFO 3338) and thus distinguished from the genus Mycobacterium. It is also distinguished from the genus Nocardia by the composition (number of carbon atoms) of mycolic acid. As the results of examination of other biochemical properties, the bacterium is recognized to be a *Rhodococcus rhodochrous*.

Microorganisms tend to undergo mutation. Accordingly, it is needless to say that the bacterium, even if it is a mutant of a competent strain such as the strain J-1, can be used in the process according to the present invention, as far as its culture product produces nitrile hydratase in the presence of a cobalt ion.

2) Substrate/nitrile

Nitriles which will be utilized as a substrate of nitrile hydratase produced by the microorganism described above are aromatic and aliphatic mononitriles or dinitriles, particularly mononitriles.

The nitriles which will best enjoy the characteristics of the present invention are aromatic nitriles, particularly those having 4 - 10 carbon atoms forming the aromatic ring. Several typical examples of the aromatic nitriles are the compounds represented by the following general formulae [I] - [VI] as follows:

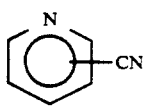
[I]

Typicals thereof are 4-, 3- and 2-cyanopyridines.

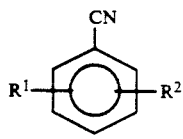
[II]

wherein $R^1$ and $R^2$, respectively, represent H, $CH_3$, OH, $OCH_3$, Cl, F, CN, $NH_2$ or $NO_2$.

Those typical thereof are benzonitrile, o-, m- and p-chlorobenzonitriles, o-, m- and p-fluorobenzonitriles, o- and m-nitrobenzonitriles, p-aminobenzonitrile, o-, m-and p-tolunitriles, 4-cyanophenol, anisonitrile, phthalonitrile, isophthalonitrile, terephthalonitrile, 2,6-dichlorobenzonitrile, 2,4-dichlorobenzonitrile, and 2,6-difluorobenzonitrile.

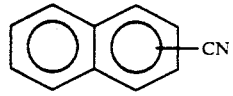
[III]

Those typical thereof are α- and β-naphthonitriles.

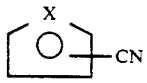
[IV]

wherein X represents S or O.

Those typical thereof are 2-thiophene carbonitrile and 2-furonitrile.

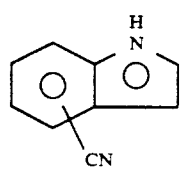
[V]

The typical example thereof is 5-cyanoindole.

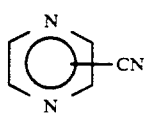
[VI]

The typical example thereof is cyanopyrazine.

Another group of nitriles forming the object of the present invention are preferably aliphatic nitriles, more preferably mono- or di-nitriles having 2 - 6 carbon atoms, most preferably mononitriles. Judging from the usefulness of the amides to be produced, acrylonitrile is typical and has a good producibility.

It goes without saying that the amides corresponding to these nitriles are those obtained by converting the CN group of the latter into a $CONH_2$ group. In the case of the dinitriles, it should be considered to be the corresponding amides obtained by converting at least one of the CN groups into a $CONH_2$ group.

3) Culturing/production of nitrile hydratase

The culturing of a microorganism in the species *Rhodococcus rhodochrous* can be conducted under any appropriate conditions provided that a cobalt ion be present in a culture medium. It may be a common practice to put an enzyme inducer which will be described in detail hereinbelow in a culture medium so that the nitrile hydrarase is accumulated in the bacterial cells.

(1) Basal medium

Examples of appropriate culture media are illustrated as follows. It can be easily performed by a person skilled in the art to vary the amount(s) of component(s) shown below, to substitute a component with another, and to eliminate some component(s) or add other component(s).

| | Component | Amount (in 1 liter of the medium) |
|---|---|---|
| (i) | Culture medium A | |
| | Vitamin mixture*[1] | 0.1 ml |
| | $K_2HPO_4$ | 13.4 g |
| | $KH_2PO_4$ | 6.5 g |
| | NaCl | 1.0 g |
| | $MgSO_4 7H_2O$ | 0.2 g |
| | Distilled water | Balance (pH 7.0) |
| | *[1]Composition: | |
| | Biotin | 2 μg |
| | Calcium pantothenate | 0.4 mg |
| | Inositol | 2 mg |
| | Nicotinic acid | 0.4 mg |
| | Thiamin hydrochloride | 0.4 mg |
| | Pyridoxine hydrochloride | 0.4 mg |
| | p-Aminobenzoic acid | 0.2 ng |
| | Riboflavin | 0.2 mg |
| | Folic acid | 0.01 ng |
| | Water | to 1 liter |
| (ii) | Culture medium B | |
| | Glycerol | 10 g |
| | Peptone | 5 g |
| | Malt extract | 3 g |
| | Yeast extract | 3 g |
| | Distilled water | Balance (pH 7.0) |
| (iii) | Culture medium C | |
| | Yeast extract | 3 g |
| | $KH_2PO_4$ | 0.5 g |
| | $K_2HPO_4$ | 0.5 g |
| | $MgSO_4 7H_2O$ | 0.5 g |
| | Distilled water | Balance (pH 7.2) |

(2) Enzyme inducer

Enzyme inducers for inducing and producing nitrile hydratase in a microorganism *Rhodococcus rhodochrous* can be any ones appropriate to the object.

Typical inducers suitable for the present invention are nitriles and amides.

The examples of enzyme inducers whose effect has been confirmed for the strain J-1 are as follows:

crotonamide, acetonitrile, propionitrile, benzamide, propionamide, acetamide, isovaleronitrile, n-butyronitrile, isobutyronitrile, n-capronitrile, 3-pentene nitrile, pivalonitrile, n-butyramide, isobutyramide, n-valeramide, n-capronamide, methacrylamide and phenylacetamide.

(3) Cobalt ion source

Nitrile hydratase is not obtained even if an enzyme inducer described above is present in a culture medium, so that it is essential in accordance with the present invention that a cobalt ion be present in the culture medium.

As the culture medium is aqueous, the cobalt ion is usually generated by adding a water soluble cobalt compound to the culture medium. The water soluble cobalt compounds are disclosed in chemical dictionaries, and thus it would be easy for the person skillful in the art to select and use an appropriate compound (in some cases, by conducting a simple preliminary test). Typical cobalt compounds are those which will give a $Co^{++}$ or a $Co^{+++}$, particularly those which will give a $Co^{++}$, and particular examples thereof are cobalt chloride, cobalt sulfate, cobalt acetate, cobalt bromide, cobalt borate or the like. Vitamin B12 and metallic cobalt are other examples of the cobalt compounds since these produce in situ a cobalt ion in the culture medium through ionization or oxidative attack by the microorganism during the culturing.

(4) Culturing

Culturing for producing and accumulating nitrile hydratase in the bacterial cell may be carried out by culturing the microorganism used, for example the strain J-1 in a culture medium as described above under an appropriate condition.

The amount of the enzyme inducer used is in the order of 2 - 6 g per 1 liter of the culture medium, and the amount of the cobalt ion is in the order of 5 - 15 mg per 1 liter of the culture medium based on $CoCl_2$.

Particular examples of the composition of the culture media are specified in the following:

| (i) | Culture medium A | 1 liter |
| | Acetonitrile (inducer) | 2 g |
| | $CoCl_2$ | 10 mg |
| (ii) | Culture medium B | 1 liter |
| | Isovaleronitrile | 2 g |
| | $CoCl_2$ | 10 mg |
| (iii) | Culture medium C | 1 liter |
| | Crotonamide | 2 g |
| | $CoCl_2$ | 10 mg |

The nitrile hydratase can be advantageously produced by the shake-culturing of the strain J-1 at a temperature from 15° to 50° C., preferably from 20° to 45° C., most preferably around 30° C. at pH 7 - 9 for ca. 30 hours or more, preferably 40 hours or more (within the upper limit of e.g. 120 hours). The enzyme inducer is preferably to be present from the initial stage of the culturing, and it is desirable for preparing bacterial cells having a high activity to supplement an inducer. For example, when shake culture is to be conducted at 28° C. for 76 hours, further amount of crotonamide is added 26 hours and 56 hours after the start of the reaction so that the concentration is 0.2% (w/v) at each time.

4) Hydration of nitrile

The premise of the present invention "process for biological production of an amide wherein a nitrile is hydrated into a corresponding amide by the action of a nitrile hydratase originated in a microorganism" includes, as described above, various reasonable embodiments or variations for the way for causing the nitrile hydratase to act on the nitrile.

One of such embodiments is to produce an amide in a culture medium while a substrate nitrile is present in a culture medium of a microorganism.

Another embodiment for causing the nitrile hydratase to act upon its substrate is to add a substrate nitrile to a culture medium in which a nitrile hydratase has been accumulated to conduct hydration reaction. The variation of the embodiment is to use a culture medium in which the cells of the microorganism have been destroyed as the "culture medium in which a nitrile hydratase has been accumulated".

A further embodiment for causing the nitrile hydratase to act upon its substrate is to isolate the cells in which the nitrile hydratase has been accumulated from a culture medium, preferably to put the cells on an appropriate carrier or "immobilize" them, and then to contact them with a substrate. This method, particularly the preferred embodiment wherein immobilized cells are used is considered to be suited for industrial use as well as or more preferentially than the second embodiments described above. This technique in which immobilized cells are used is well known in the art as to the kind of the carrier, the method for immobilizing the microorganism in a carrier and the utilization of the immobilized microorganism in a so-called bioreactor.

Another embodiment for the nitrile hydratase to act upon its substrate is the method wherein an enzyme preparation of a nitrile hydratase is prepared and wherein a nitrile is hydrated by the enzyme preparation in rather a non-biological way. It goes without saying that the hydration reaction in this way should be conducted under such pH and temperature conditions that the enzyme activity will not be lost. Such conditions can be said to be the same as those in the above described "biological way". As described above, the embodiment in which microorganisms are not present during the action of the enzyme is also treated as a "biological production process" in the present invention.

According to the present invention, nitrile hydratase has an appropriate pH range for it of from 7 to 9 with the optimal pH for it of 8.0. If the reaction solution shows a pH of less than 7, the activity of the enzyme tends to decrease abruptly. Accordingly, it is desirable to add a buffer to the reaction solution. Even if any one of the buffers such as a potassium phosphate buffer, a Tris/HCl buffer, a HEPES/KOH buffer and a sodium borate buffer is used, the enzyme activity of the nitrile hydratase will not be varied.

The concentration of the substrate in the culture medium or in the hydration reaction solution is ordinarily in the range of 4 to 7 moles/liter, and the reaction temperature is usually in the range of 10° to 30° C.

3. Experimental Examples

The method for measuring the activity of nitrile hydratase and the unit of activity in the experimental examples below are defined as follows:

(1) Method for measuring the activity of nitrile hydratase

The activity of nitrile hydratase is measured by carrying out the reaction with 2 ml of a reaction mixture which contains 10 mM of benzonitrile, 30 mM of a potassium phosphate buffer (pH 7.0) and a certain amount of the cells of a microorganism (isolated from a culture medium) at 10° C. for 5 minutes and adding 2 ml of 1N-HCl to stop the reaction.

(2) Definition of unit

One unit (U) of nitrile hydratase activity is defined as the amount of an enzyme required for producing benzamide from benzonitrile under the above described condition at a rate of 1 μmole/min.

REFERENTIAL EXAMPLE 1

The J-1 strain was cultured using a culture medium of which composition is specified below under the culturing conditions which are also specified below, and the expression of the nitrile hydratase activity is examined by adding $CoCl_2$ and/or $FeSO_4$ to the culture medium during culture.

| Ingredient | Amount (in 1 liter of medium) |
| --- | --- |
| (i) Composition of culture medium | |
| Vitamin mixture | 3.0 ml |
| $K_2HPO_4$ | 0.5 g |
| $KH_2HPO_4$ | 0.5 g |
| $MgSO_4 7H_2O$ | 0.5 g |
| Propionitrile | 2 ml |
| Distilled water | Balance (pH 7.2) |
| (ii) Culture condition | |
| 28° C./70–80 hours | |

The results obtained are shown below.

It can be seen that the nitrile hydratase activity will not be developed even if $FeSO_4$ is added to the basic medium, the nitrile hydratase activity is developed when $CoCl_2$ is added, and the addition of $FeSO_4$ to the system to which $CoCl_2$ has been added, will adversely affect the results.

*1 Amount of cells: based on the dry weight.
*2 U: Unit of activity according to the definition above, and the amount of cells are based on the dry weight.

REFERENTIAL EXAMPLE 2

The effects of various nitriles or amides as an enzyme inducer on the strain J-1 are set forth in the table below.

The results set forth in the table below are those obtained by preliminarily culturing the strain J-1 in the aforementioned culture medium B at 28° C., adding a nitrile or an amide as an inducer in an amount of 0.1% (v/v) or 0.2% (w/v), respectively, when the strain has proliferated sufficiently, and further inoculating the strain into the aforementioned culture medium C to which 0.001% (w/v) of $CoCl_2$ has been added to culture the microorganism for 36 to 48 hours.

| | Specific activity (U/mg) | Total activity (U/ml) | Amount of cells (mg of dry cells/ml) |
| --- | --- | --- | --- |
| Crotonamide | 2.22 | 4.48 | 2.02 |
| Acetonitrile | 1.41 | 3.47 | 2.46 |
| Propionitrile | 1.36 | 4.44 | 3.26 |
| Benzamide | 0.84 | 2.75 | 3.26 |
| Propionamide | 0.79 | 2.29 | 2.90 |
| Acetamide | 0.71 | 1.55 | 2.18 |
| n-Butyronitrile | 1.40 | 0.38 | 3.70 |
| Isobutyronitrile | 0.41 | 1.24 | 3.06 |
| Isovaleronitrile | 0.34 | 1.05 | 3.07 |
| n-Capronitrile | 0.28 | 1.04 | 3.71 |
| 3-Pentene nitrile | 0.32 | 1.42 | 4.49 |
| Pivalonitrile | 0.35 | 0.24 | 0.69 |
| n-Butyroamide | 0.43 | 1.55 | 3.62 |
| Isobutyramide | 0.09 | 0.33 | 3.48 |
| Isovaleramide | 0.44 | 1.08 | 1.81 |
| n-Capronamide | 0.30 | 1.06 | 3.52 |
| Methacrylamide | 0.20 | 0.62 | 3.12 |
| Phenylacetamide | 0.29 | 0.28 | 0.95 |

EXAMPLE 1

The cells of the strain J-1 obtained by culturing the strain in a culture medium comprising the aforementioned culture medium C containing $CoCl_2$ and crotonamide added thereto, in respective proportions of 0.01 g and 2 g per liter of the medium was reacted with a variety of nitriles used as the substrate. The reaction was conducted using 2 ml of a reaction solution comprising the cells obtained from 2 ml of the culture, 10 mM of a potassium phosphate buffer (pH 8.0) and 200 mM of the substrate at 25° C. for 76 hours. The reaction was stopped by adding thereto 0.2 ml of 1N-HCl. The nitrile hydratase activities to the respective substrates are set forth as the ratios of the reaction product or the spent amount of the substrate measured by HPLC to the nitrile hydratase activity measured with 3-cyanopyridine as the substrate, that is the specific activity (%).

The results are shown below.

| Substrate | Specific activity (%) |
| --- | --- |
| 3-Cyanopyridine | 100 |
| Acrylonitrile | 106 |
| 4-Cyanopyridine | 129 |
| 2-Cyanopyridine | 64 |
| 5-Cyanoindole | 9 |
| 2-Thiophene carbonitrile | 116 |
| 2-Furonitrile | 71 |
| Benzonitrile | 80 |
| 4-Cyanophenol | 24 |
| p-Aminobenzonitrile | 16 |
| m-Nitrobenzonitrile | 7 |

| | Metal ion added | | | | | | | | | |
| --- | --- | --- | --- | --- | --- | --- | --- | --- | --- | --- |
| $CoCl_2$ (mg) | 0 | 0 | 0 | 0 | 0 | 10 | 10 | 10 | 10 | 10 |
| $FeSO_4$ (mg) | 0 | 5 | 10 | 20 | 40 | 0 | 5 | 10 | 20 | 40 |
| Amount of cells*1 (mg/ml) | 1.06 | 1.14 | 1.25 | 1.24 | 1.34 | 2.04 | 1.90 | 2.16 | 2.16 | 2.07 |
| | Enzyme activity | | | | | | | | | |
| U/mg of cells*2 | 0 | 0 | 0 | 0 | 0 | 0.59 | 0.26 | 0.34 | 0.32 | 0.16 |
| U/ml of medium | 0 | 0 | 0 | 0 | 0 | 1.2 | 0.49 | 0.73 | 0.69 | 0.33 |

-continued

| Substrate | Specific activity (%) |
|---|---|
| o-Nitrobenzonitrile | 16 |
| m-Chlorobenzonitrile | 29 |
| p-Tolunitrile | 5 |
| o-Tolunitrile | 46 |
| m-Tolunitrile | 32 |
| Anisonitrile | 20 |
| o-Chlorobenzonitrile | 41 |
| p-Chlorobenzonitrile | 7 |
| 2,4-Dichlorobenzonitrile | 2 |
| 2,6-Dichlorobenzonitrile | 1 |
| Cyanopyrazine | 80 |

EXAMPLE 2

In a 1-liter Sakaguchi flask was placed 400 ml of a culture medium comprising the aforementioned culture medium C containing $CoCl_2$ and crotonamide added thereto, respectively, in a proportion of 0.01 g and 2 g per liter of the medium, and the mixture was cultured on a shaking apparatus at 28° C. Culture was continued with further addition to the culture medium of 0.2% (w/v) of crotonamide (800 mg/400 ml) at 30 hours and 60 hours after the initiation of culture, and was stopped at 80 hours after the initiation of culture.

The bacterial cells were collected by centrifuging the culture medium under 12,000 g for 15 minutes with a centrifugal separator (Hitachi model SCR 20 B), washed with 0.85% NaCl, centrifuged again, and suspended into 40 ml of the above described solution. A small portion of the suspension was sampled and used for measuring the dry weight of the bacterial cells in the suspension.

The suspension containing cells (corresponding to 2.33 mg of the dry cells) was added to 4 ml of a reaction solution which contained 10 mM of potassium phosphate buffer (pH 8.0) and 4.57 M of 3-cyanopyridine, and the reaction was conducted at 25° C. overnight with adding to the reaction solution 0.55 M and 0.49 M of 3-cyanopyridine, after 3 and 6 hours from the initiation of the reaction, respectively. The yield of the nicotinamide produced was 5.58 M after 18 hours from initiation of reaction. Accordingly, the conversion reached 99.5%, which corresponds to the accumulation of nicotinamide in an amount of 681 g. At this concentration, the reaction product solidified as the result of the deposition of the nicotinamide.

The nicotinamide thus produced was identified by isolating the product as crystals and analyzing it by elementary analysis, IR, NMR and mass spectrometry. Nicotinic acid was not detected.

EXAMPLE 3

The suspension containing cells (corresponding to 2.33 mg of the dry cells) obtained in Example 2 was added to 4 ml of a reaction solution which contained 10 mM of potassium phosphate buffer (pH 8.0) and cyanopyrazine in a variety of concentrations. The reaction was conducted at 25° C. Four moles of cyanopyrazine were converted into pyrazinamide with a conversion of 100% after a 6-hour reaction, and six moles of cyanopyrazine after a 9-hour reaction. On the other hand, when a suspension which contains the bacterial cells in an amount corresponding to 4.66 mg of the dry weight in place of 2.33 mg of the dry weight described above, was added to the similar reaction solution (4 ml), 7 M of the cyanopyrazine was converted into pyrazinamide with a conversion of 100% after a 6-hour reaction, and 8 M of cyanopyrazine after a 9-hour reaction. Production of pyrazinecarboxylic acid was not recognized.

The pyrazinamide was crystallized from the solution as it was produced. The crystalline deposit was directly collected and recrystallized from methanol. The crystals were identified as pyrazinamide by analyzing them by elementary analysis, IR, NMR and mass spectrometry.

Analysis of cyanopyrazine, pyrazinamide and pyrazinecarboxylic acid was conducted by means of high performance liquid chromatography.

The same analysis as in this example was also conducted in the following examples.

EXAMPLE 4

The suspension of the bacterial cells (corresponding to 4.66 mg of the dry cells) obtained in Example 2 was added to 4 ml of the reaction solution containing 10 mM of a potassium phosphate buffer (pH 8.0) and 3 M of methacrylonitrile, and the reaction was conducted at 25° C. with adding 3 M of methacrylonitrile to the reaction solution after 1 hour and 3 hours from the initiation of the reaction, respectively. After 12 hours from the initiation of the reaction, 9 M of methacrylamide was produced with a 100% conversion.

In the above reaction, when an addition 1 M of methacrylonitrile was added 5 hours after the initiation of the reaction, 10 M of methacrylamide was produced in a conversion of 100% 24 hours after the initiation of the reaction. The concentration of 10 M corresponds to that 851 g of methacrylamide was produced and accumulated per 1 liter of the reaction solution.

The reaction solution was diluted with water, and the bacterial cells were removed by centrifugal treatment (under 12,000 g for 15 minutes). The cell-free solution was concentrated on a rotary evaporator and crystallized. Then the crystals were dissolved in and recrystallized from water to obtain the crystals of methacrylamide.

EXAMPLE 5

The suspension of the bacterial cells (corresponding to 4.66 mg of the dry cells) obtained in Example 2 was added to 4 ml of the reaction solution containing 10 mM of a potassium phosphate buffer (pH 8.0) and 1 M of crotonitrile, and the reaction was conducted at 25° C. with the addition of 1 M portions of methacrylonitrile to the reaction solution five times in total with an interval of 1 hour after the initiation of the reaction. After 6 hours from the initiation of the reaction, 6 M of crotonamide was produced in a conversion of 100%. When additional 1 M portions of crotonitrile were added to the reaction solution after 6 hours and 10 hours from the initiation of the reaction, respectively, 7 M and 8 M of crotonamide were produced in a conversion of 100%, after 10 hours and 22 hours, respectively. The concentration of 8 M corresponds to that 681 g of crotonamide was produced and accumulated per 1 liter of the reaction solution.

The crystallization of crotonamide was conducted in the same manner as in Example 4.

EXAMPLE 6

The suspension of the bacterial cells (corresponding to 4.66 mg of the dry cells) obtained in Example 2 was added to 4 ml of the reaction solution containing 10 mM of a potassium phosphate buffer (pH 8.0) and 3 M of acetonitrile, and the reaction was conducted at 25° C. with the addition of 3 M portions of acetonitrile to the reaction solution 1 hour and 3 hours after the initiation of the reaction and 5 M of acetonitrile 6 hours after the initiation of the reaction. After 12 hours from the initiation of the reaction, 14 M of acetamide was produced in a conversion of 100%. In other words, 827 g of acetamide was produced and accumulated per 1 liter of the reaction solution.

The reaction solution was diluted with water and subjected to centrifugal treatment to remove the bacterial cells. The supernatant was concentrated to dryness on a rotary evaporator, dissolved in methanol and then crystallized from methanol to obtain the crystals of acetamide.

EXAMPLE 7

The suspension of the bacterial cells (corresponding to 4.66 mg of the dry cells) obtained in Example 2 was added to 4 ml of the reaction solution containing 10 mM of a potassium phosphate buffer (pH 8.0) and 3 M of 3-hydroxypropionitrile, and the reaction was conducted at 25° C. with the addition of 3 M portions of 3-hydroxypropionitrile to the reaction solution four times in total with an interval of 1 hour after the initiation of the reaction. After 5 hours from the initiation of the reaction, 15 M of 3-hydroxypropionamide was produced in a conversion of 100%. When additional 3 M portions of 3-hydroxypropionitrile was added to the reaction solution at this stage, 18 M of 3-hydroxypropionamide was produced in a conversion of 100% after 11 hours from the initiation of the reaction. This means that 1600 g of 3-hydroxypropionamide was produced and accumulated per 1 liter of the reaction solution.

The reaction solution was diluted with water and subjected to centrifugal treatment to remove the bacterial cells. The cell-free supernatant was then concentrated on a rotary evaporator and crystallized at a temperature of −20° C. The crystals were dissolved in isopropanol and recrystallized from the solvent to obtain the crystals of 3-hydroxypropionamide.

EXAMPLE 8

In a 1-liter Sakaguchi Flask was placed 400 ml of a culture medium comprising the aforementioned culture medium C containing $CoCl_2$ and crotonamide added thereto, respectively, in a proportion of 0.01 g and 2 g per liter of the medium, and the mixture was cultured on a shaking apparatus at 28° C. Culture was continued with further addition to the culture medium of 0.2% (w/v) of crotonamide (800 mg/400 ml) at 26 hours and 56 hours after the initiation of culture, and was stopped at 76 hours after the initiation of culture.

The bacterial cells were collected by centrifuging the culture medium under 10,000 g for 20 minutes with a centrifugal separator (Hitachi model SCR 20B), washed with 0.85 NaCl, centrifuged again, and suspended into 40 ml of the above described solution. A small portion of the suspension was sampled and used for measuring the dry weight of the bacterial cells in the suspension.

The suspension containing cells (corresponding to 2.96 mg of the dry cells) was added to 4 ml of a reaction solution which contained 10 mM of potassium phosphate buffer (pH 8.0) and 3-cyanopyridine in a variety of concentrations. The reaction was conducted at 25° C. Eight moles of 3-cyanopyridine were converted into nicotinamide with a conversion of 100% after a 9 hour reaction, and nine moles of 3-cyanopyridine after a 22 hour reaction. On the other hand, when a suspension which contains the bacterial cells in an amount corresponding to 5.92 mg of the dry weight in place of 2.96 mg of the dry weight described above, was added to the similar reaction solution (4 ml), 9 M of the 3-cyanopyridine was converted into nicotinamide with a conversion of 100% after a 5-hour reaction, and 12 M of 3-cyanopyridine after a 9-hour reaction. Production of nicotinic acid was not recognized.

The concentration of 12 M corresponds to that 1,465 g of nicotinamide was produced and accumulated per 1 liter of the reaction solution.

The nicotinamide was crystallized from the solution as it was produced. The crystals were collected and recrystallized from methanol.

EXAMPLE 9

The suspension of the bacterial cells (corresponding to 5.92 mg of the dry cells) obtained in Example 8 was added to 4 ml of the reaction solution containing 10 mM of a potassium phosphate buffer (pH 8.0) and 1 M of benzonitrile, and the reaction was conducted at 25° C. with adding 1 M of benzonitrile to the reaction solution after 1,2,3,4,5 and 7 hours from the initiation of the reaction, respectively. After 24 hours from the initiation of the reaction, 7 M (848g/lit.) of benzamide was produced with a 100% conversion.

EXAMPLE 10

The suspension of the bacterial cells (corresponding to 5.92 mg of the dry cells) obtained in Example 8 was added to 4 ml of the reaction solution containing 10 mM of a potassium phosphate buffer (pH 8.0) and 0.5 M of 2,6-difluorobenzonitrile, and the reaction was conducted at 25° C. with adding 0.5 M of 2,6-difluorobenzonitrile to the reaction solution after 2,4,6 and 8 hours from the initiation of the reaction, respectively. After 22 hours from the initiation of the reaction, 2.5 M (393 g/lit.) of 2,6-difluorobenzamide was produced with a 100% conversion.

EXAMPLE 11

The suspension of the bacterial cells (corresponding to 5.92 mg of the dry cells) obtained in Example 8 was added to 4 ml of the reaction solution containing 10 mM of a potassium phosphate buffer (pH 8.0) and 1 M of 2-thiophene carbonitrile, and the reaction was conducted at 25° C. with adding 1 M of 2-thiophene carbonitrile to the reaction solution after 1 hour from the initiation of the reaction. After 5 hours from the initiation of the reaction, 2 M (254 g/lit.) of 2-thiophene carboxamide was produced with a 100% conversion.

EXAMPLE 12

The suspension of the bacterial cells (corresponding to 5.92 mg of the dry cells) obtained in Example 8 was added to 4 ml of the reaction solution containing 10 mM of a potassium phosphate buffer (pH 8.0) and 1 M of 2-furonitrile, and the reaction was conducted at 25° C. with adding 1 M of 2-furonitrile to the reaction solution after 1,2,4,6,8,11 and 23 hours from the initiation of the reaction, respectively. After 30 hours from the initiation of the reaction, 8 M (888 g/lit.) of 2-furane carboxamide was produced with a 100% conversion.

EXAMPLE 13

The suspension of the bacterial cells (corresponding to 5.92 mg of the dry cells) obtained in Example 8 was added to 4 ml of the reaction solution containing 10 mM of a potassium phosphate buffer (pH 8.0) and 4 M of 3-indoleacetonitrile, and the reaction was conducted at 25° C. After 24 hours from the initiation of the reaction, 4 M (697 g/lit.) of 3-indoleacetamide was produced with a 100% conversion.

What is claimed is:

1. In a process for biological production of an amide, wherein a nitrile selected from an aromatic nitrile having 4 – 10 carbon atoms in the aromatic nucleus and an aliphatic nitrile having 2 – 6 carbon atoms is hydrated into the corresponding amide by the action of a nitrile hydratase present in a microorganism, the improvement which comprises contacting said nitrile with cells of the microorganism *Rhodococcus rhodochrous* J-1 which has been cultured in the presence of cobalt ion contained in a culture medium in an amount of about 5 to 15 mg per liter, calculated as $CoCl_2$ and in the presence of about 2 to 6 g per liter of an amide or nitrile inducer capable of inducing nitrile hydratase and wherein the culture medium is essentially free of iron ions, to thereby produce nitrile hydratase in said *Rhodococcus rhodochrous* J-1 and recovering the amide produced.

2. The process for biological production of an amide according to claim 1, wherein said aromatic nitrile is selected from the group consisting of:

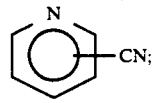 [I]

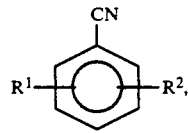 [II]

wherein $R^1$ and $R^2$, respectively, represent H, $CH_3$, OH, $OCH_3$, Cl, F, CN, $NH_2$ or $NO_2$;

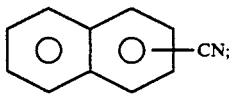 [III]

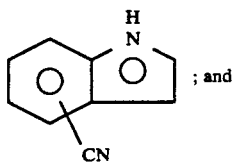 [IV]

wherein X represents S or O;

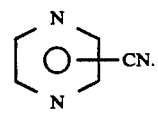 [V]

; and

[VI]

3. The process for biological production of an amide according to claim 2, wherein said aromatic nitrile is 2-cyanopyridine, 3-cyanopyridine or 4-cyanopyridine.

4. The process for biological production of an amide according to claim 3, wherein said aromatic nitrile is 3-cyanopyridine.

5. The process for biological production of an amide according to claim 2, wherein said aromatic nitrile is cyanopyrazine.

6. The process for biological production of an amide according to claim 1, wherein said aliphatic nitrile having 2 – 6 carbon atoms is acrylonitrile.

7. The process for biological production of an amide according to claim 1, wherein the inducer capable of inducing nitrile hydratase is selected from a member of the group consisting of propionitrile, crotonamide, isovaleronitrile and acetonitrile.

8. A method for producing cells having high nitrile hydratase activity which is useful for converting a nitrile to an amide, comprising culturing the microorganism *Rhodococcus rhodochrous* J-1 in a culture medium containing cobalt ion in an amount of about 5 to 15 mg per liter, calculated as $CoCl_2$ and about 2 to 6 g per liter of an amide or nitrile inducer capable of inducing nitrile hydratase and wherein the culture medium is essentially free of iron ions, to thereby produce nitrile hydratase in said *Rhodococcus rhodochrous* J-1 and separating cells of said *Rhodococcus rhodochrous* J-1 from said culture medium.

9. The method for producing cells having high nitrile hydratase activity according to claim 8, wherein the inducer capable of inducing nitrile hydratase is selected from a member of the group consisting of propionitrile, crotonamide, isovaleronitrile and acetonitrile.

* * * * *